United States Patent [19]

Bach et al.

[11] 4,001,242

[45] Jan. 4, 1977

[54] D-6-METHYL-8-FORMYL-10α-ALKOXY-8-ERGOLENE

[75] Inventors: Nicholas J. Bach; Edmund C. Kornfeld, both of Indianapolis, Ind.

[73] Assignee: Eli Lilly and Company, Indianapolis, Ind.

[22] Filed: Aug. 4, 1975

[21] Appl. No.: 601,740

Related U.S. Application Data

[62] Division of Ser. No. 494,149, Aug. 2, 1974, Pat. No. 3,923,812.

[52] U.S. Cl. .............................. 260/285.5; 424/261
[51] Int. Cl.² ...................................... C07D 457/02
[58] Field of Search ................................ 260/285.5

[56] References Cited

UNITED STATES PATENTS

| | | | |
|---|---|---|---|
| 3,732,231 | 5/1973 | Semonsky et al. | 260/285.5 |
| 3,814,765 | 6/1974 | Bernardi et al. | 260/285.5 |
| 3,904,634 | 9/1975 | Arcari et al. | 260/285.5 |

FOREIGN PATENTS OR APPLICATIONS

| | | | |
|---|---|---|---|
| 459,243 | 1968 | Switzerland | 260/285.5 |

OTHER PUBLICATIONS

Lin et al.; J. Org. Chem. vol. 38, pp. 2249–2251 (1973).

*Primary Examiner*—Donald G. Daus
*Assistant Examiner*—Mary C. Vaughn
*Attorney, Agent, or Firm*—James L. Rowe; Everet F. Smith

[57] ABSTRACT

Elymoclavine is prepared by oxidation of D-6-methyl-8-hydroxymethyl-10α-methoxy-8-ergolene to the corresponding D-8-aldehyde followed by reduction with an active metal in acid medium.

1 Claim, No Drawings

D-6-METHYL-8-FORMYL-10α-ALKOXY-8-ERGOLENE

This is a division of application Ser. No. 494,149, filed Aug. 2, 1974, now U.S. Pat. No. 3,923,812.

BACKGROUND OF THE INVENTION

Compounds based on the ergoline ring system (I):

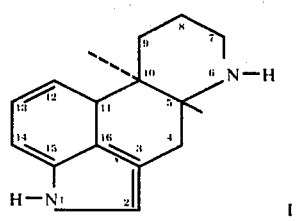

have a surprising variety of pharmaceutical activities. For example, lysergic and isolysergic acid are D-8-carboxy-6-methyl-Δ⁹-ergolines (9,10-didehydroergolines or 9-ergolenes.) The amides of lysergic acid have valuable and unique pharmacologic properties, and include the naturally-occurring peptide alkaloids; ergocornine, ergokryptine, ergonovine, ergocristine, ergosine, ergotamine, etc., synthetic oxytocic alkaloids such as methergine, and the synthetic hallucinogen lysergic acid diethylamide or LSD. Ergotamine, a 9-ergolene, with a "peptide" side chain, has been used in the treatment of migraine and recently, both ergocornine and 2-bromo-α-ergokryptine have been shown to be inhibitors of prolactin and of dimethylbenzanthracene (DMBA)-induced tumors in rats, according to Nagasawa and Meites, Proc. Soc. Exp'tl. Bio. Med. 135, 469 (1970) and to Heuson et al., Europ. J. Cancer, 353 (1970). (See also U.S. Pat. Nos. 3,752,888 and 3,752,814).

Non-peptide ergot derivatives, both naturally occurring and totally or partially synthetic, share these multiple pharmacological properties with the peptide derivatives. For example, D-6-methyl-8-cyanomethylergoline, was prepared by Semonsky and co-workers, Coll, Czech. Chem. Commun., 33, 577 (1968), and was found to be useful in preventing pregnancy in rats — Nature, 221, 666 (1969), (See also U.S. Pat. No. 3,732,231) — by interfering with the secretion of hypophysial leuteotropic hormone and the hypophysial gonadotropins or by inhibiting the secretion of prolactin. [See Seda et al., Reprod. Fert., 24, 263 (1971) and Mantle and Finn, id. 441)]. Semonsky and co-workers, Coll, Czech, Chem. Comm., 36, 220 (1971), have also prepared D-6-methyl-8-ergolinylacetamide, a compound which is stated to have anti-fertility and anti-lactating effects in rats. The 2-halo derivatives of D-6-methyl-8-cyanomethylergoline and of D-6-methyl-8-ergolinylacetamide have been prepared and tested for their prolactin inhibiting activity (M. J. Sweeney, J. A. Celmens, E. C. Kornfeld and G. A. Poore, 64th Annual Meeting Amer. Assoc. Cancer Research, April, 1973).

A number of the non-peptide indole alkaloids have been found in fungus cultures grown on Elymus nollis and other related grasses. These non-peptide alkaloids include chanoclavine, agroclavine, elymoclavine, and penniclavine. Of particular interest are agroclavine, an 8-methyl-8-ergolene; elymoclavine, an 8-hydroxymethyl-8-ergolene; and penniclavine, a 8-hydroxymethyl-8-hydroxy-9-ergolene. These non-peptide alkaloids have been shown to have potent rat prolactin inhibiting activity comparable to that found with the peptide alkaloid, ergocornine. The synthesis of penniclavine from D-6-methyl-8-hydroxymethyl-10α-methoxyergolene has been disclosed by Bernardi and Temperilli at the 9th Symposium on the Chemistry of Natural Products, International Union of Pure and Applied Chemistry held at Ottawa, Province of Ontario, Canada, June 24–28, 1974.

It is an object of this invention to provide a synthesis of elymoclavine from optically active starting materials. Other objects of this invention will become apparent from the specification which follows.

SUMMARY OF THE INVENTION

This invention provides a process for the synthesis of elymoclavine which comprises the oxidation of a D-6-methyl-8-hydroxymethyl-10α-alkoxy ergolene to yield a D-6-methyl-8-formyl-10α-alkoxy ergolene represented by Structure II below. Reduction of this 8-formyl derivative under conditions which eliminate the alkoxy group gives elymoclavine (Structure III below) in excellent yield. The above synthetic procedure is illustrated by the following Reaction Scheme 1.

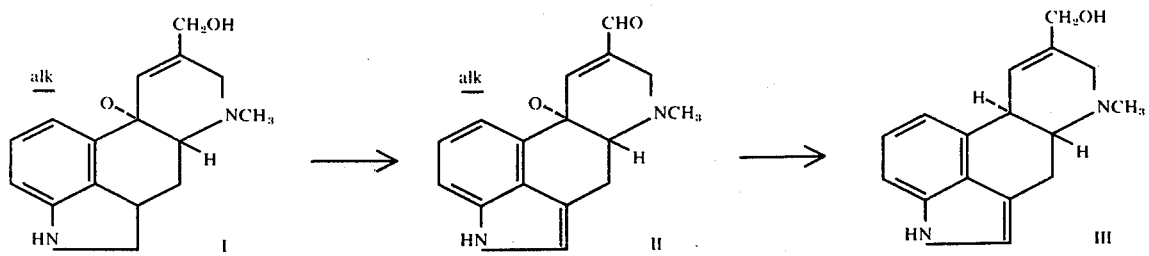

in which alk is (C₁-C₃) alkyl, as for example, methyl, ethyl, isopropyl or n-propyl.

In Reaction Scheme 1, above, the procedure of going from the primary alcohol (I) to the corresponding aldehyde (II) can be carried out with a variety of oxidative procedures. For example, sodium dichromate in a mixture of pyridine hydrochloride and pyridine, chromic oxide-pyridine complex in methylene dichloride, potassium dichromate in aqueous sulfuric acid, t-butyl chromate in benzene, nickel peroxide in benzene, silver carbonate in benzene or silver oxide in phosphoric and acetic acids, manganese dioxide in a variety of solvents, lead tetra-acetate in pyridine, sulfur trioxide-pyridine complex in a mixture of dimethyl sulfoxide and triethylamine, tetrachloro-1,2-benzoquinone (TCBQ) and the like can all be employed [see Compendium of Organic Synthetic Methods, Harrison and Harrison, (John Wiley and Sons, Inc., New York, 1971) Section 48 at page 137-143. We prefer to employ manganese dioxide in chloroform or other suitable inert solvent as the oxidizing agent to prepare the aldehyde (II) from the primary alcohol (I). An alternate oxidizing procedure which gives similarly excellent yields consists of using dicyclohexylcarbodiimide in a solvent consisting of a mixture of dimethylsulfoxide, pyridine and trifluoroacetic acid. The second step of the above synthetic procedure, the reduction of the 8-formyl-10α-alkoxy-8-ergolene with the concomitant elimination of the 10α-alkoxy group can also be accomplished by a variety of reagents. We prefer to employ an active metal in an acidic medium as for example, zinc in acetic acid. Iron in dilute hydrochloric acid can also be employed as can the metal hydride reducing agents as exemplified by lithium aluminum hydride and lithium aluminum (tri-t-butyloxy) hydride. This specification is further illustrated by the following specific example.

EXAMPLE

SYNTHESIS OF ELYMOCLAVINE

A solution containing 515 mg. of D-6-methyl-8-hydroxy-methyl-10α-methoxy-8-ergolene in 150 ml. of chloroform was prepared. 4 g. of manganese dioxide were added and the reaction mixture stoppered and stirred at room temperature for one-half hour. The reaction mixture was filtered, and the filter cake washed with chloroform. Evaporation of the filtrate to dryness yielded a residue of D-6-methyl-8-formyl-10α-methoxy-8-ergolene formed in the above reaction. The residue was chromatographed over a 30 g. of florisil using chloroform containing 1 to 2 percent methanol as the eluant. Fractions shown to contain the 8-formyl compound by thin layer chromatography were combined and the solvent evaporated therefrom. Recrystallization of the resulting residue yielded purified D-6-methyl-8-formyl-10α-methoxy-8-ergolene melting at 196°–7° C. with decomposition.

Analysis Calc.: C, 72.32; H, 6.43; N, 9.92; Found: C, 72.07; H, 6.20; N, 9.65.

A solution was prepared containing 300 mg. of D-6-methyl-8-formyl-10α-methoxy-8-ergolene in 25 ml. of acetic acid. 2 g. of zinc dust were added and the reaction mixture stirred at room temperature for 45 minutes. The reaction mixture was filtered and the filtrate poured over ice. The aqueous layer was made strongly basic with 10 percent aqueous ammonium hydroxide, and the alkali-insoluble organic material extracted with chloroform. The chloroform extractions were continued until a chloroform extract showed a negative Van Urk test. The chloroform extracts were combined and washed with saturated aqueous sodium chloride. Evaporation of the organic solvent yielded elymoclavine.

D-6-methyl-8-formyl-10α-methoxy-8-ergolene can also be prepared by contacting D-6-methyl-8-hydroxymethyl-10α-methoxy-8-ergolene in dimethylsulfoxide solution with a mixture of pyridine and trifluoroacetic acid. Dicyclohexylcarbodimide is then added and the primary alcohol group oxidized to an aldehyde according to the procedure of Moffatt J. Am. Chem. Soc., 89, 2697 (1967). D-6-methyl-8-formyl-10α-methoxy-8-ergolene prepared by this procedure was purified by chromatography and crystallized as in the above example.

A 10α-ethoxy or 10α-propoxy derivative can be employed in place of D-6-methyl-8-hydroxymethyl-10α-methoxy-8-ergolene of the above example. These D-6-methyl-8-hydroxy-methyl-10α-alkoxy-8-ergolenes are prepared by the reduction of a D-6-methyl-8-carbomethoxy-10α-alkoxy-8-ergolene as furnished by the procedure of U.S. Pat. No. 3,814,765. According to this procedure, methyl lysergate is reacted with a mercuric salt, such as mercuric acetate in a lower aliphatic alcohol for a period from 2–24 hours at a temperature from 0° to 50° C. After the reaction had been completed the excess salt is decomposed by the addition of sodium borohydride. The 10α-alkoxy group will be derived from the particular lower alkanol employed in the mercuric salt reaction. The 8-carbomethoxy group is then converted to the corresponding primary alcohol by reduction with a metal hydride reducing agent preferably sodium bis (2-methoxyethoxy) aluminum hydride. This latter reaction is set forth in greater detail in the copending application of Kornfeld and Bach, Ser. No. 494,147 filed Aug. 2, 1974, now U.S. Pat. No. 3,929,796.

Elymoclavine, the product of the above synthetic procedure is a prolactin inhibitor and gives a 71 percent inhibition of prolactin at a 10 mcg. level in the following test: Adult male rats of th Spraque-Dawley strain weighing about 200 g. were used. All rats were housed in an air-conditioned room with controlled lighting (lights on 6 a.m. - 8 p.m.) and fed lab chow and water ad libitum. In each experiment the rats were killed by decapitation, and 150 μl aliquots of serum were assayed for prolactin. Each male rat received an intraperitoneal injection of 2.0 mg of reserpine in aqueous suspension 18 hours before administration of elymoclavine. The purpose of the reserpine was to keep prolactin levels uniformly elevated. The elymoclavine was dissolved in 10% ethanol at a concentration of 10 mcg/ml, and were injected intraperitoneally at a standard dose of 50 mcg/kg. Each compound was administered to a group of 10 rats, and a control group of 10 intact males received an equivalent amount of 10 percent ethanol. One hour after treatment, all rats were killed by decapitation, and the serum was collected and assayed for prolactin as previously described. The results were evaluated statistically using Student's "t" test to calculate the level of significance, "p". The difference between the prolactin level of the treated rats and prolactin level of the control rats, divided by the prolactin level of the control rats gave the percent inhibition of prolactin secretion attributable to elymoclavine.

As a prolactin inhibitor, elymoclavine is potentially useful in the treatment of inappropriate lactation such as postpartum lactation and galactorrhea. In addition, it can be used to treat prolactin-dependent adenocarcinomas and prolactin-secreting pituitary tumors as well as the following disorders: Forbes — Albright syndrome, Chiari-Frommel syndrome, gynecomastia itself and gynecomastia occurring as a result of estrogenic steroid administration for prostatic hypertrophy, fibrocystic disease of the breast (benign nodules), prophylactic treatment of breast cancer, and breast development resulting from the administration of psychotropic drugs, for example, thorazine, or for prostatic hypertrophy itself.

In employing elymoclavine to inhibit prolactin secretion, the compound or a salt thereof with a pharmaceutically-acceptable acid is suspended in corn oil and the suspension injected parenterally or fed to a female mammal in amounts varying from 0.01 to 10 mg/kg/day of mammalian weight. Oral administration is preferred. If parenteral administration is used, the injection is preferably by the subcutaneous route using an appropriate pharmaceutical formulation although other modes of parenteral administration such as intraperitoneal, intramuscular, or intravenous administration are equally effective. In particular, with intravenous or intramuscular administration, a soluble pharmaceutically-acceptable salt of elymoclavine preferably the methanesulfonate or maleate salt, is customarily employed. For oral administration, the compound either as the free base or in the form of a salt thereof can also be mixed with standard pharmaceutical excipients and loaded into empty telescoping gelatin capsules or pressed into tablets.

We claim:

1. D-6-methyl-8-formyl-10α-alkoxy-8-ergolene of the formula

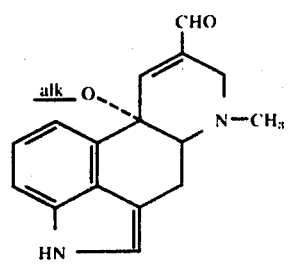

wherein alk is $(C_1-C_3)$ alkyl.

* * * * *